United States Patent [19]

Shiba

[11] Patent Number: 5,066,794
[45] Date of Patent: Nov. 19, 1991

[54] PROCESS FOR PREPARING A DISACCHARIDE DERIVATIVE

[75] Inventor: Tetsuo Shiba, Osaka, Japan

[73] Assignee: Daiichi Pharmaceutical Co., Ltd., Tokyo, Japan

[21] Appl. No.: 471,064

[22] Filed: Jan. 29, 1990

Related U.S. Application Data

[63] Continuation of Ser. No. 342,639, Apr. 19, 1989, abandoned, which is a continuation of Ser. No. 769,289, Aug. 26, 1985, abandoned.

[51] Int. Cl.$^5$ .................... C07H 5/06; C07H 1/02
[52] U.S. Cl. ..................... 536/55.3; 536/53; 536/117; 536/4.1; 536/17.1; 536/17.2
[58] Field of Search ............... 536/53, 55.3, 117, 17.1, 536/4.1, 17.2

[56] References Cited

U.S. PATENT DOCUMENTS 4,495,346  1/1985  Anderson et al. .................. 536/53

FOREIGN PATENT DOCUMENTS 8404526  11/1984  PCT Int'l Appl. .................. 536/53

OTHER PUBLICATIONS

Galanos et al.; Chemical Abstracts, vol. 100: 169643f, May 21, 1984.
Imoto et al.; Chemical Abstracts, vol. 100: 82458a, Mar. 12, 1984.
Kanegasaki et al.; Chemical Abstracts, vol. 101: 185675a, Nov. 19, 1984.
Qureshi et al.; Journal of Biological Chemistry, 258(21), 12947-12951, Nov. 10, 1983.
Imoto et al.; Tetrahedron Letters, 25(25): 2667-2670 (1984).
Kusumoto et al.; Tetrahedron Letters, 25(34): 3727-3730 (1984).
Kotani, S. et al.; Infection and Immunity, vol. 49:1 (225-237), Jul. 1985.
Galanos et al.; Eur. J. Biochem, vol. 140(2): 221-227, Apr. 1984.

Primary Examiner—Ronald W. Griffin
Assistant Examiner—Nancy S. Carson
Attorney, Agent, or Firm—Sughrue, Mion, Zinn, Macpeak & Seas

[57] ABSTRACT

Disaccharide derivatives represented by the formula (I):

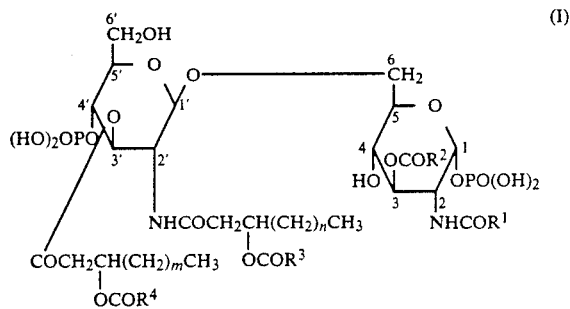

wherein $R^1CO-$ and $R^2CO-$ each represents a residue of a straight chain fatty acid having from 8 to 20 carbon atoms and having a hydroxyl group at the 3-position thereof; $R^3CO-$ and $R^4CO-$ each represents a residue of a straight chain fatty acid having from 8 to 20 carbon atoms; and m and n each represents an integer of from 8 to 12, and the salts thereof. The compounds exhibit biological activities equal to or higher than those of natural lipid A. Also, the compounds of this invention are very useful as standard reagent for determination of endotoxin in the samples to be tested.

3 Claims, No Drawings

PROCESS FOR PREPARING A DISACCHARIDE DERIVATIVE

This is a continuation of application Ser. No. 07/342,639 filed Apr. 19, 1989, now abandoned, which is a continuation of application Ser. No. 06/769,289 filed Aug. 26, 1985, now abandoned.

FIELD OF THE INVENTION

This invention relates to novel disaccharide derivatives represented by the formula (I):

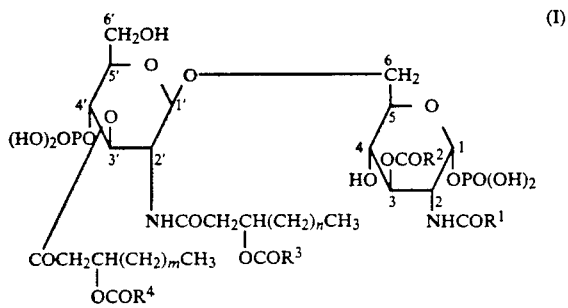

wherein $R^1CO-$ and $R^2CO-$ each represents a residue of a straight chain fatty acid having from 8 to 20 carbon atoms and having a hydroxyl group at the 3-position thereof; $R^3CO-$ and $R^4CO-$ each represents a residue of a straight chain fatty acid having from 8 to 20 carbon atoms; and m and n each represents an integer of from 8 to 12, and the salts thereof.

BACKGROUND OF THE INVENTION

It is known that endotoxin which is an outer membrane component of various Gram negative bacilli has various biological activities, such as enhancement of immune function of an animal. The main active portion of the endotoxin is considered to reside in a disaccharide moiety which is one of units constituting lipopolysaccharide, and establishment or presumption of structures of disaccharide moiety of various Gram negative bacilli has been studied. For example, the structure of the disaccharide moiety of Salmonella typhimurium was established as reported in J. Biol. Chem., 258, 12801 to 12803 (1983), and the presumed structure of the disaccharide moiety of Escherichia coli was reported in Tetrahedron Lett., 24, 4017–4020 (1983).

In parallel to these studies, various disaccharide derivatives having structures similar to the established or presumed structures of the natural disaccharide compounds (hereinafter referred to as natural lipid A) have been synthesized, and their biological activities, such as immunological activity, have been examined. However, any of these synthetic disaccharide derivatives (hereinafter referred to as synthetic lipid A) lacks biological activities or has, if any, far less activity as compared with natural lipid A extracted from E. coli (Infec. Immun., 45, 293–296 (1984) and Eur. J. Biochem., 140, 221–227 (1984).)

The above described differences between the natural lipid A and the synthetic lipid A on biological activities are believed to arise from differences of fatty acid residues bonded to the 2'-amino group and 3'-hydroxyl group of a non-reducing end of glucosamine. More specifically, in the known synthetic lipid A, a straight chain fatty acid residue or a straight chain fatty acid residue having a hydroxyl group at the 3-position is bonded to the 2'-amino group and the 3'-hydroxyl group of the non-reducing end of glucosamine. Whereas, in the natural lipid A, it is presumed that a straight chain fatty acid residue having a hydroxyl group at the 3-position is bonded to the 2'-amino group and the 3'-hydroxyl group, and the fatty acid moiety has a straight chain fatty acid residue bonded to the 3-hydroxyl group thereof through an ester linkage. Lipid A extracted from E. coli has not yet been isolated and identified as a single component. (Nihon Saikingaku Zasshi, 39 (3), 295 and 463 (1984))

SUMMARY OF THE INVENTION

Based on the above described presumption, the present inventor has synthesized compounds represented by the formula (I) that can be regarded to have the closest chemical structure to that of natural lipid A and completed this invention. Natural lipid A exhibits a mitogenic activity, i.e., an activity to stimulate lymphocytes to promote production of neolymphocytes and enhancing immune function, a tumor necrosis factor (TNF)-inducing activity, and the like. Therefore, the compounds of this invention are useful for prophylaxis and treatment of many diseases caused by reduced immune function, for example, as preventing and treating agents for various infectious diseases, various cancer, etc.

Since the novel compounds according to the present invention are considered to have a chemical structure similar to that of natural lipid A as described above, it is reasonable that they possess biological activities equal or superior to those of natural lipid A. Further, as being single pure compounds, they are possibly free from various disadvantages associated with natural lipid A.

The utilities of the compounds of the present invention as pharmaceutical agents have been confirmed by the mitogenicity and the TNF-inducing activity, as described hereinafter in Test Examples 1 and 2.

Also, the compounds of this invention are very useful as a standard reagent for determination of endotoxin in the samples to be tested, and their activity has been confirmed by the local Shwartzman reaction test (Test I in Test Example 3), the pyrogenicity test (Test II in Test Example 3), and the activation of clotting enzyme of Tachypleus tridentatus (horseshoe crab) amoebocytes, i.e., Limulus test (Test III in Test Example 3).

The local Shwartzman reaction test (Test I) is examined to determine the phenomenon of necrosis, at the site where a test compound was injected, induced by intravenous injection of lipopolysaccharide (hereinafter referred to as LPS) after 20 hours from intracutaneous injection of the test compound to test animals, preferably in rabbits. When the test compound shows a positive reaction (necrosis) in this test, it can be considered to have the endotoxin specific activity. LPS and natural lipid A which have been conventionally used as standard reagents for determination of endotoxin exhibit positive reactions in this test.

Tests II and III have been used for determining endotoxin in the samples to be tested.

As described hereinafter in detail in Test Examples 1 to 3, a known synthetic lipid A exhibits negative reactions in Tests I and II and thus does not satisfy the requirements for standard reagent for determination of endotoxin, whereas natural lipid A and LPS exhibit positive reactions in these tests.

Accordingly, the positive reaction shown by the compounds of this invention in Tests I to III proves that these compounds are useful as standard reagents for determination of endotoxin.

Further, the conventional standard reagents for determination of endotoxin are natural products extracted from bacteria and are not always uniform in their purity and activity, whereas the compounds of the present invention do not have such disadvantages since these compounds can be synthetically prepared as a product having a constant activity.

DETAILED DESCRIPTION OF THE INVENTION

The compounds represented by the formula (I) of the present invention can be prepared according to the following reaction route involving Steps A to E:

by the formula (III) to obtain a compound represented by the formula (IV).

Step B comprises removing TCEC groups bonded to the 2'-amino group and the 6'-hydroxyl group of the compound (IV) and, at the same time, bonding a group represented by the formula (VI):

$$-COCH_2CH(CH_2)_nCH_3 \quad (VI)$$
$$\quad\quad\quad |$$
$$\quad\quad\quad OCOR^3$$

wherein $R^3CO-$ and n are as defined above, to the 2'-amino group.

Step C comprises protecting the 6'-hydroxyl group of the resulting compound with, for example, a benzyloxymethyl group.

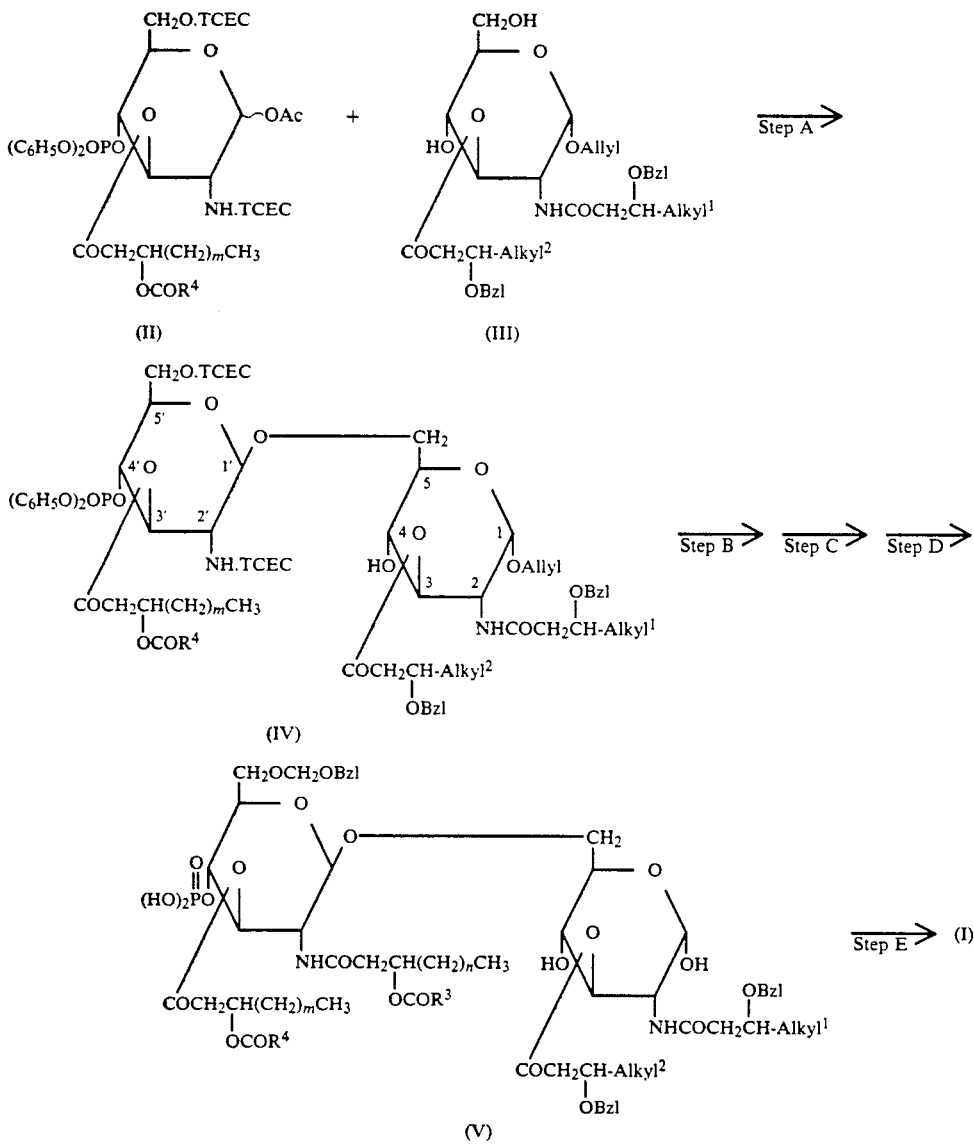

wherein TCEC represents a trichloroethoxycarbonyl group; Allyl represents an allyl group; Ac represents an acetyl group; Bzl represents a benzyl group; Alkyl[1] and Alkyl[2] each represents an alkyl group having from 5 to 17 carbon atoms; and $R^3CO-$, $R^4CO-$, m and n are as defined above.

Step A comprises condensating a compound represented by the formula (II) with a compound represented Step D comprises removing the protecting allyl group at the 1-hydroxyl group to obtain the compound represented by the formula (V).

Finally, Step E comprises reacting the compound (V) with dibenzyl phosphorochloridate to introduce a phosphono group into the 1-hydroxyl group and then removing all the protecting groups for functional groups by catalytic reduction to obtain the desired compound of the present invention.

Reaction conditions for Steps A to E are generally as follows.

Step A

The compound represented by the formula (II) is dissolved in an inert solvent, such as anhydrous methylene chloride, and the O-acetyl group is replaced with a bromine atom by treating the solution with dry hydrogen bromide gas under ice-cooling. After the solvent is removed, the resulting compound is dissolved in an anhydrous reaction solvent, e.g., methylene chloride, chloroform, etc., and condensed with the compound of the formula (III) in the presence of mercury (II) cyanide, silver carbonate or silver oxide, preferably mercury (II) cyanide, and in the presence of a dehydrating agent, e.g., anhydrous calcium sulfate, under heating at about 70° C. for about 24 to 38 hours. The reaction mixture is treated with a 5% potassium iodide aqueous solution and then purified by silica gel column chromatography to obtain the disaccharide compound (IV).

Step B

The disaccharide compound (IV) is dissolved in acetic acid, and a zinc powder is added to the solution, followed by allowing the mixture to react at room temperature for several tens minutes, preferably 30 minutes, to remove the protecting group at the 2'-amino group. Then, the resulting product is acylated with a desired fatty acid, e.g., (R)—3—dodecanoyloxytetradecanoic acid, in the presence of a condensing agent commonly employed for peptide synthesis, e.g., dicyclohexylcarbodiimide, etc., and preferably in the presence of a base, e.g., ethylisopropylamine, 4-dimethylaminopyridine, etc., and the product is purified by silica gel column chromatography.

Step C

The compound obtained in Step B is dissolved in anhydrous chloroform or anhydrous methylene chloride, preferably the latter, and benzyloxymethyl chloride and a base, e.g., pyridine, ethyldiisopropylamine, etc., are added to the solution at room temperature to react for about 48 hours. Purification by silica gel column chromatography gives a compound of which 6'-hydroxyl group is protected with a benzyloxymethyl group.

Step D

The compound obtained in Step C is dissolved in tetrahydrofuran, and an iridium complex such as Ir(-COD)[PCH$_3$(C$_6$H$_5$)$_2$]$_2$PF$_6$ (wherein COD represents cyclooctadiene) is added thereto. The mixture is allowed to react at about 45° C. for several tens minutes, preferably 40 minutes. Water and iodine are added to the reaction mixture at room temperature, and the reaction is continued for several minutes, preferably about 10 minutes. Purification of the reaction product by silica gel column chromatography gives the compound (V).

Step E

The compound (V) is dissolved in an anhydrous aprotic solvent, e.g., anhydrous tetrahydrofuran, and a 10 w/v % butyl lithium solution in hexane is added thereto at −70° C. After about 5 minutes, benzyl phosphorochloridate is added to the reaction mixture, followed by continuing the reaction for about several tens minutes, preferably about 20 minutes. The reaction mixture is then subjected to catalytic reduction to remove all the protecting groups for functional groups. The reaction product is purified by silica gel column chromatography and then desalted by electrodialysis to obtain the desired compound (I) of this invention.

The compounds represented by the formulae (II) and (III) which can be used as starting materials for the synthesis of the compounds of this invention are novel and can be prepared by the process shown in Reference Examples hereinafter described.

The present invention will now be illustrated in greater detail with reference to the following Reference Examples and Example, but it should be understood that the present invention is not limited thereto. In these examples, all percents and ratios are by weight unless otherwise indicated.

REFERENCE EXAMPLE 1

(1) Thirty grams of D-glucosamine hydrochloride was dissolved in 500 ml of water, and 30.0 g of sodium hydrogen carbonate was added thereto, followed by cooling in an ice bath. To the cooled solution was added 27.5 ml of trichloroethoxycarbonyl chloride, and the mixture was stirred under ice-cooling for 2 hours and then at room temperature for 11 hours. The precipitate was collected by filtration, washed successively with water and diethyl ether, and recrystallized from 95% ethanol to obtain 42.3 g of N-trichloroethoxycarbonyl-D-glucosamine (Compound A) having a melting point of 183° to 184° C. (with decomposition).

Elementary Analysis for C$_9$H$_{14}$NO$_7$Cl$_3$.0.5H$_2$O: Calcd. (%): C 29.73, H 4.16, N 3.85, Cl 29.25. Found (%): C 29.98, H 4.19, N 3.88, Cl 29.20.

(2) In 230 ml of 2 w/v % dry hydrogen chloride in absolute allyl alcohol was suspended 35.0 g of Compound A, and the suspension was heated for 20 minutes on an oil bath at 100° C. with stirring. After allowing the mixture to cool to room temperature, the solvent was removed by distillation under reduced pressure. Toluene was added to the residue, followed by distillation under reduced pressure. This distillation operation was repeated three times. The finally obtained residue was dissolved in 400 ml of anhydrous acetone, and 35 g of anhydrous calcium sulfate was added thereto, followed by stirring for a while. To the reaction mixture were added 38 ml of 2,2-dimethoxypropane and 4.0 g of p-toluenesulfonic acid, and the stirring was continued at room temperature for 3.5 hours. The reaction mixture was neutralized with a saturated aqueous solution of sodium hydrogen carbonate, and any insoluble material was removed by filtration. The solvent was removed by distillation under reduced pressure, and the residue was dissolved in chloroform, washed successively with a saturated aqueous solution of sodium hydrogen carbonate and water, and dried over sodium sulfate. The solvent was removed by distillation under reduced pressure, and the residue was recrystallized from 99% ethanol-ethyl acetate to obtain 17.5 g of allyl 2-deoxy-4,6-O-isopropylidene-2-trichloroethoxycarbonylamino-α-D-glucopyranoside (Compound B) having a melting point of 185° to 187° C.

$[\alpha]_D^{33}$ +72.5° (c 1.1, acetone)

Elementary Analysis for C$_{15}$H$_{22}$NO$_7$Cl$_3$: Calcd. (%): C 41.45, H 5.10, N 3.22, Cl 24.47. Found (%): C 41.57, H 4.93, N 3.20, Cl 24.07.

(3) Thirteen grams of Compound B, 10.0 g of (R)-3-benzyloxytetradecanoic acid and 0.73 g of 4-dimethylaminopyridine were dissolved in 250 ml of anhydrous chloroform, and 6.17 g of dicyclohexylcarbodiimide (DCC) was added to the solution. The resulting mixture was stirred at room temperature for 1 hour, followed by filtration to separate any insoluble material. The solvent was removed by distillation under reduced pressure, and the residue was purified by passing through a column packed with 500 g of silica gel while eluting with chloroform-acetone with the acetone content being gradually increased to obtain 14.5 g of allyl 2-deoxy-4,6-O-isopropylidene-2-trichloroethoxycarbonylamino-3-O-[(R)-3-benzyloxytetradecanoyl]-α-D-glucopyranoside (Compound C) as a colorless oily product.

(4) In 290 ml of acetic acid was dissolved 14.5 g of Compound C, and 29 g of a zinc powder was added thereto. The resulting mixture was stirred at room temperature for 1.5 hours, and the insoluble material was removed by filtration. The solvent was removed by distillation under reduced pressure. Toluene was added to the residue and then distilled off under reduced pressure. The residue was dissolved in chloroform, washed successively with 0.1 N hydrochloric acid and water, and dried over anhydrous magnesium sulfate. The solvent was removed by distillation under reduced pressure, and the residue was dissolved in 100 ml of chloroform. The solution was neutralized with triethylamine, and the chloroform was distilled off under reduced pressure. The remaining oily product was dissolved in 250 ml of anhydrous chloroform, and 7.75 g of (R)-3-benzyloxytetradecanoic acid and 4.78 g of DCC were added thereto, followed by stirring at room temperature for 30 minutes. Any insoluble material was removed by filtration, and the solvent was removed by distillation under reduced pressure. The residue was dissolved in 225 ml of acetic acid, and 25 ml of water was added thereto while heating on a boiling water bath. The heating was continued for 30 minutes, and the reaction mixture was allowed to cool to room temperature, followed by distillation under reduced pressure to remove the solvent. Toluene was added to the residue and then distilled off under reduced pressure. This distillation operation was repeated twice, and the residue was purified by silica gel column chromatography (silica gel: 500 g; eluent: chloroformacetone=5:1). Recrystallization of the crude product from hexane gave 9.53 g of allyl 2-deoxy-2-[(R)-3-benzyloxytetradecanoylamino]-3-O-[(R)-3-benzyloxytetradecanoyl]-α-D-glucopyranoside (Compound D: the compound of the formula (III)) as colorless crystals having a melting point of 80° to 82° C.

Elementary Analysis for $C_{51}H_{81}NO_9$: Calcd. (%): C 71.88, H 9.58, N 1.64. Found (%): C 71.85, H 9.67, N 1.62.

REFERENCE EXAMPLE 2

(1) Ten grams of Compound B prepared in Reference Example 1-(2) and 11.5 g of (R)-3-tetradecanoyloxytetradecanoic acid were dissolved in 350 ml of anhydrous methylene chloride, and 1.4 g of 4-dimethylaminopyridine and 5.2 g of DCC were added thereto, followed by stirring at room temperature for 2 hours. To the reaction mixture was added 1.5 ml of acetic acid to decompose the excess DCC, and the insoluble material was removed by filtration. The filtrate was washed successively with 1 N hydrochloric acid and water, dried, and distilled under reduced pressure to remove the solvent. The residue was purified by silica gel column chromatography (silica gel: 500 g; eluent: chloroform-acetone=30:1), and the product was suspended in 200 ml of 90% acetic acid. The suspension was heated in a hot water bath at 90° C. for 10 minutes, followed by allowing the mixture to cool to room temperature. The solvent was removed by distillation under reduced pressure. Toluene was added to the residue and distilled off under reduced pressure. This distillation operation was repeated 3 times, and the finally obtained residue was recrystallized from hexane to obtain 12.7 g of allyl 2-deoxy-2-trichloroethoxycarbonylamino-3-O-[(R)-3-tetradecanoyloxytetradecanoyl]-α-D-gluco-pyranoside (Compound E) having a melting point of 68° to 70° C.

(2) In 60 ml of pyridine was dissolved 2.7 g of Compound E, and 0.89 ml of trichloroethoxycarbonyl chloride was added thereto under ice-cooling, followed by stirring for 20 minutes in an ice bath. Water was added to the reaction mixture and, after stirring at room temperature for a while, the solvent was removed by distillation under reduced pressure. The residue was dissolved in chloroform, washed successively with 1 N hydrochloric acid, water, a saturated aqueous solution of sodium hydrogen carbonate and water, and dried over anhydrous magnesium sulfate. The solvent was removed by distillation under reduced pressure, and the residue was purified by silica gel column chromatography (silica gel: 100 g; eluent: chloroform-acetone=30:1) to obtain 2.0 g of a 6-O-trichloroethoxycarbonyl ester of Compound E (Compound F) as a colorless oily product.

(3) Two grams of Compound F was dissolved in 60 ml of anhydrous methylene chloride. To the solution were added 0.24 ml of pyridine, 0.36 g of 4-dimethylaminopyridine and 0.62 ml of diphenyl phosphorochloridate, and the resulting mixture was stirred at room temperature for 2 hours. The reaction mixture was washed successively with 1 N hydrochloric acid, water, a saturated aqueous solution of sodium hydrogen carbonate and water, dried over magnesium sulfate, and distilled under reduced pressure to remove the solvent. The residue was purified by silica gel column chromatography (silica gel: 90 g; eluent: chloroform-acetone=90:1) to obtain 2.2 g of allyl 6-O-trichloroethoxycarbonyl-2-deoxy-2-trichloroethoxycarbonylamino-3-O-[(R)-3-tetradecanoyloxytetradecanoyl]-4-O-diphenylphosphono-α-D-glucopyranoside (Compound G) as a colorless oily product.

(4) In 40 ml of degassed tetrahydrofuran was dissolved 2.2 g of Compound G, and 73 mg of Ir(COD)[PCH$_3$(C$_6$H$_5$)$_2$]$_2$PF$_6$ (wherein COD represents cyclooctadiene) was added to the solution. The atmosphere of the system was replaced with hydrogen. After confirming that the red color of the iridium complex disappeared, the atmosphere was again degassed and then replaced with nitrogen. The mixture was stirred at 45° C. for 40 minutes, followed by allowing to cool to room temperature. Eight milliliters of water and 0.9 g of iodine were added thereto, and the resulting mixture was stirred at room temperature for 10 minutes. A 5% aqueous solution of sodium sulfite was added thereto until the color of iodine disappeared, and the mixture was extracted with chloroform. The organic layer was washed with water and dried over anhydrous magnesium sulfate. The solvent was removed by distillation under reduced pressure, and the residue was purified by silica gel column chromatography (silica gel: 90 g; eluent: chloroform-acetone=20:1) to obtain 1.45 g of a compound having a free hydroxyl group at the 1-position of Compound G (Compound H) as an oily product.

(5) In 120 ml of chloroform was dissolved 9.9 g of Compound H, and 3.3 ml of pyridine and 3.9 ml of acetic anhydride were added to the solution to acetylate at room temperature. The reaction mixture was treated in a usual manner, and the crude product was recrystalized from hexane to give 8.0 g of 1-acetylated Compound H (Compound J; the compound of the formula (II)) having a melting point of 77° to 80° C.

$[\alpha]_D^{29}$ +35.6° (c 0.55, chloroform)

Elementary Analysis for $C_{54}H_{78}NO_{16}Cl_6P$: Calcd. (%): C 52.27, H 6.34, N 1.13, Cl 17.14. Found (%): C 52.32, H 6.31, N 1.13, Cl 17.34.

EXAMPLE (1) In 800 ml of anhydrous methylene chloride was dissolved 3.94 g of Compound J prepared in Reference Example 2. After the solution was saturated with dry hydrogen bromide gas under ice-cooling, the system was closed, and the mixture was allowed to stand at room temperature overnight. The solvent was removed by distillation under reduced pressure. Toluene was added thereto and then distilled off under reduced pressure. This distillation operation was repeated twice, and the remaining oily product was dried over potassium hydroxide in a desiccator under reduced pressure. The resulting oily product was dissolved in 200 ml of anhydrous chloroform, and 1.35 g of Compound D prepared in Reference Example 1-(4), 1.60 g of mercury (II) cyanide and 4 g of anhydrous calcium sulfate were added to the solution. The mixture was stirred at reflux in an oil bath at 70° C. After stirring for 20 hours, additional 1.35 g of Compound D was added thereto, and the stirring was further continued for 18 hours at reflux. Any insoluble material was removed by filtration, and the filtrate was washed successively with a 5% aqueous solution of potassium iodide and water, dried over anhydrous magnesium sulfate, and distilled under reduced pressure to remove the solvent. Purification of the residue by silica gel column chromatography (silica gel: 110 g; eluent: chloroform-acetone=15:1) gave 4.54 g of allyl 6-O-{2-deoxy-2-trichloroethoxycarbonylamino-3-O-[(R)-3-tetradecanoyloxytetradecanoyl]-4-O-diphenylphosphono-6-O-trichloroethoxycarbonyl-β-D -glucopyranosyl}-2-deoxy-2-[(R)-3-benzyloxytetradecanoylamino]-3-O-[(R)-3-benzyloxytetradecanoyl]-α-D-glucopyranoside (Compound K) as a colorless oily product.

Elementary Analysis for $C_{103}H_{155}N_2O_{23}Cl_6P$: Calcd. (%): C 60.85, H 7.68, N 1.38, Cl 10.46. Found (%): C 60.74, H 7.69, N 1.29, Cl 10.70.

(2) In 140 ml of acetic acid was dissolved 4.48 g of Compound K, and 9.0 g of a zinc powder was added to the solution. The resulting mixture was stirred at room temperature for 30 minutes, followed by filtration to separate any insoluble material. The filtrate was distilled under reduced pressure, and the residue was reacted with 1.13 g of (R)-3-dodecanoyloxytetradecanoic acid and 0.55 g of DCC in the same manner for the synthesis of Compound D as described in Reference Example 1-(4). The reaction product was purified by silica gel column chromatography (silica gel: 150 g; eluent: chloroformacetone=9:1) to obtain 3.25 g of allyl 6-O-{2-deoxy-2-[(R)-3-dodecanoyloxytetradecanoylamino]-3-O-[(R)-3-tetradecanoyloxytetradecanoyl]-4-O-diphenylphosphono-β-D-glucopyranosyl}-2-deoxy-2-[(R)-3-benzyloxytetradecanoylamino]-3-O-[(R)-3-benzyloxytetradecanoyl]-α-D-glucopyranoside (Compound L) as a colorless oily product. A portion of the oily product was dissolved in dioxane and lyophilized, and the resulting solid was subjected to elementary analysis.

Elementary Analysis for $C_{123}H_{201}N_2O_{22}P\cdot H_2O$: Calcd. (%): C 70.05, H 9.70, N 1.33. Found (%): C 69.97, H 9.62, N 1.43.

(3) In 100 ml of anhydrous methylene chloride was dissolved 3.14 g of Compound L, and 0.35 g of benzyloxymethyl chloride and 0.39 ml of ethyldiisopropylamine were added to the solution, followed by stirring at room temperature. After stirring for 24 hours, 0.35 g of benzyloxymethyl chloride and 0.39 ml of ethyldiisopropylamine were added thereto. After 41 hours, the same compounds were supplemented in amounts of 0.24 g and 0.26 ml, respectively. After the stirring was continued for a total period of 48 hours, the reaction mixture was washed with 1N hydrochloric acid and then with water, dried, and distilled under reduced pressure to remove the solvent. Purification of the residue by silica gel column chromatography (silica gel: 180 g; eluent: chloroform-acetone=15:1) gave 2.17 g of Compound L of which 6'-hydroxyl group was protected with a benzyloxymethyl group (Compound M) as a colorless oily product. A portion of the oily product was dissolved in dioxane and lyophilized, and the resulting solid was subjected to elementary analysis.

Elementary Analysis for $C_{131}H_{209}N_2O_{23}P\cdot 0.5H_2O$: Calcd. (%): C 70.87, H 9.53, N 1.26. Found (%): C 70.80, H 9.56, N 1.30.

(4) In 60 ml of degassed tetrahydrofuran was dissolved 2.11 g of Compound M, and 0.11 g of the same iridium complex as used in the synthesis of Compound H (Reference Example 2-(4)), and then 5 ml of water and 0.50 g of iodine were added to the reaction system to conduct reaction in the same manner as for the synthesis of Compound H. After a 5% aqueous solution of sodium sulfite was added to the reaction mixture until the color of iodine disappeared, the mixture was extracted with chloroform. The chloroform layer was washed successively with a 5% aqueous solution of sodium sulfite and water, dried and distilled under reduced pressure to remove the solvent. The residue was dissolved in a mixture of 50 ml of chloroform, 5 ml of methanol and 1 ml of acetic acid, followed by allowing the solution to stand overnight. The solvent was again distilled off under reduced pressure, and the residue was purified by silica gel column chromatography (silica gel: 80 g; eluent: chloroformacetone=10:1) to obtain 1.31 g of 6-O-{2-deoxy-2-[(R)-3-dodecanoyloxytetradecanoylamino]-3-O- [(R)-3-tetradecanoyloxytetradecanoyl]-4-O-diphenylphosphono-6-O-benzyloxymethyl-β-D-glucopyranosyl}-2-deoxy-2-[(R)-3-benzyloxytetradecanoylamino]-3-O-[(R)-3-benzyloxytetradecanoyl]-α-D-glucopyranose (Compound N) as a pale yellow solid. A portion of the resulting solid was dissolved in dioxane and lyophilized, and the resulting solid was subjected to elementary analysis.

Elementary Analysis for $C_{128}H_{205}N_2O_{23}P\cdot 0.5H_2O$: Calcd. (%): C 70.52, H 9.52, N 1.29. Found (%): C 70.40, H 9.44, N 1.33.

(5) Six hundred milligrams of Compound N was dissolved in 10 ml of anhydrous tetrahydrofuran, and the solution was cooled to −70° C. in a dry ice-alcohol bath. To the cooled solution was added 0.21 ml of a 10 W/V % hexane solution of butyl lithium while stirring. After 5 minutes, 85 μl of dibenzyl phosphorochloridate was dissolved therein by shaking, followed by stirring at the same temperature for 20 minutes. To the cooled reaction mixture was added 600 mg of palladium black, and the resulting mixture was catalytically reduced at room temperature in a hydrogen stream at a pressure of 8 atm. while stirring. After 2 hours, the palladium black was separated by filtration. Three hundred milligrams of platinum oxide was added to the filtrate, and the mixture was further stirred in a hydrogen stream at a pressure of 8 atm. for 3 hours, followed by filtration to remove the catalyst. The solvent was removed by distillation under reduced pressure, and the residue was purified by silica gel column chromatography (silica gel: 80 g; eluent: chloroform-methanol-water-triethylamine = 10:5:1:0.05). The crude product was dispersed in 10 ml of water, and the dispersion was subjected to electrodialysis using a cellophane membrane at a voltage of 200 to 300 V for 4 hours while adding a 1M triethylamine acetate solution and maintaining the pH value at 9 by occasionally adding triethylamine. The non-dialyzable fraction was adjusted to pH 9 with triethylamine and then dissolved in water. Dilute hydrochloric acid was added to the solution, and the thus formed precipitate was collected by centrifugation to obtain 137 mg of 6-O-{2-deoxy-2-[(R)-3-dodecanoyloxytetradecanoylamino]-3-O-[(R)-3-tetradecanoyloxytetradecanoyl]-4-O-phosphono-$\beta$-D-glucopyranosyl}-2-deoxy-2-[(R)-3-hydroxytetradecanoylamino]-3-O-[(R)-3-hydroxytetradecanoyl]-1-O-phosphono-$\alpha$-D-glucopyranose.

Elementary Analysis for $C_{94}H_{178}N_2O_{25}P_2.3H_2O$: Calcd. (%): C 60.95, H 10.01, N 1.51. Found (%): C 61.04, H 10.05, N 1.46.

The activities of the compounds of this invention are hereinafter described in detail with reference to Test Examples. Test compounds used in these test examples are as follows:

Compound of Present Invention

6-O-{2-Deoxy-2-[(R)-3-dodecanoyloxytetradecanoylamino]-3-O-[(R)-3-tetradecanoyloxytetradecanoyl]-4-O-phosphono-$\beta$-D-glucopyranosyl}-2-deoxy-2-[(R)-3-hydroxytetradecanoylamino]-3-O-[(R)-3-hydroxytetradecanoyl]-1-O-phosphono-$\alpha$-D-glucopyranose.

Control Compound 1

6-O-{2-Deoxy-2-[(R)-3-hydroxytetradecanoylamino]-3-O-[(R)-3-hydroxytetradecanoyl]-4-O-phosphono-$\beta$-D-glucopyranosyl}-2-deoxy-2-[(R)-3-hydroxytetradecanoylamino]-3-O-[(R)-3-hydroxytetradecanoyl]-1-O-phosphono-$\alpha$-D-glucopyranose.

Control Compound 2

Lipid A extracted from *E. coli* 08:K27, Re-mutant (strain F515).

Control Compound 3

LPS extracted from *E. coli* 08: K27, Re-mutant (strain F515).

TEST EXAMPLE 1

Test on Mitogenicity

The mitogenicity of the compounds of this invention was determined in terms of stimulation of [$^3$H]-labeled thymidine uptake into, for example, isolated murine lymphocytes (splenocytes). Spleen of BALB/c nu/nu mice (male; 8-week old) was minced, and lymphocytes collected from the minced spleen were incubated with graded doses of test compounds in RPMI 1640 medium without fetal bovine serum at 37° C. at a concentration of $1 \times 10^5$ to $1 \times 10^6$ lymphocytes per ml for 48 hours. Twenty-four hours before the completion of the incubation, [$^3$H]-labeled thymidine (manufactured by New England Nuclear) was added to the culture. After the completion of the incubation, cells were collected on glass microfiber paper and dried, and the radioactivity of [$^3$H]-labeled thymidine incorporated into the cells was measured. The ratio of thymidine uptake in the test culture to which the test compound had been added to that in the respective control culture was determined as a stimulation index. The higher the stimulation index, the higher the mitogenicity. The results obtained are shown in Table 1.

TABLE 1

| Test Compound | Amount of Test Compound Added ($\mu$g/ml) | Stimulation Index ± S.E. |
|---|---|---|
| Compound of Present Invention | 1 | 11.76 ± 0.13 |
|  | 0.1 | 9.05 ± 0.70 |
|  | 0.01 | 4.06 ± 0.35 |

TEST EXAMPLE 2

TNF-Inducing Activity

The TNF-inducing activity of the compounds of this invention was determined by administering the test compound to BCG-primed mice and measuring cytostatic and cytocidal actions of test sera from the mice on L-929 cells (originated in mice fibroblast). That is, ICR mice (female; 5-week old) were primed by intravenous inoculation of $1.3 \times 10^8$ viable units of BCG vaccine (Japan BCG Laboratory, Tokyo) per mouse, and, 2 weeks after the priming, 10 $\mu$g of the test compound was administered intravenously to each mouse. Ninety minutes later, blood samples were obtained and sera were prepared.

On the other hand, each well of a 96-well microculture plate (manufactured by Corning Glass Works) was filled with 90 $\mu$l (containing $3 \times 10^4$ cells) of a suspension of L-929 cells, grown and suspended in Eagle's minimal essential medium (MEM) supplemented with 10% fetal bovine serum (manufactured by Flow Laboratories Inc., Va.), 100 U/ml of penicillin, 100 $\mu$g/ml of streptomycin and 2% Meylon (manufactured by Otsuka Pharmaceutical Co., Tokushima, Japan). Two hours later, 100 $\mu$l of the above-prepared serum samples which had been serially diluted 5 folds with the above-described medium and then [$^3$H]-labeled thymidine were added to each well. After incubation for 48 hours at 37° C., cells were collected by centrifugation, and radioactivity of [$^3$H]-labeled thymidine incorporated into the cells was determined. A reciprocal of the final dilution of the test serum that resulted in 50% inhibition of [$^3$H]-labeled thymidine uptake of L-929 cells was calculated by the Kärber method and referred to as TNF-inducing activity (ED$_{50}$). The results obtained are shown in Table 2 below.

TABLE 2

| Test Compound | TNF-Inducing Activity ED$_{50}$ |
|---|---|
| Compound of Present Invention | 2,692 |

TABLE 2-continued

| TNF-Inducing Activity | |
|---|---|
| Test Compound | $ED_{50}$ |
| Control Compound 1 | 2,198 |
| Control Compound 2 | 3,981 |
| Control Compound 3 | 4,753 |

TEST EXAMPLE 3

Test on Endotoxin

Test I—Local Shwartzman Reaction Induction Activity

The test on Shwartzman reaction specific to endotoxin was carried out as follows using Japanese white rabbits (female, weighing around 3 kg). That is, Japanese domestic white rabbits were intracutaneously injected with the test compound. Twenty hours later, 100 μg of LPS extracted from Salmonella minnesota R595, Re-mutant was intravenously injected to each rabbit. The Shwartzman reaction-induction activity was expressed in terms of number of animals that suffered from hemorrhagic necrosis at the site that had been prepared by intracutaneous injection of the test compound. The results obtained are shown in Table 3 below.

TABLE 3

| Shwartzman Reaction-Induction Activity | | |
|---|---|---|
| Test Compound | Dose (μg/site) | Number of Necrosed Animals/Number of Tested Animals |
| Compound of Present Invention | 20 | 2/3 |
| Control Compound 1 | 80 | 0/3 |
| Control Compound 2 | 20 | 3/3 |
| Control Compound 3 | 20 | 3/3 |

Test II—Test on Pyrogenicity

The pyrogenicity of the compounds of this invention was determined in terms of body temperature increase in rabbits after intravenous injection of the test compound in accordance with the test method of pyrogenicity defined in Japanese Pharmacopoeia. That is, the rectal temperatures of Japanese domestic white rabbits (body weight: 2 to 2.5 kg) were measured 3 times at one-hour intervals. When the temperature in the second and third measurements were substantially equal, the third temperature was taken as a reference temperature. Within 15 minutes after the third measurement, the test compound dissolved in pyrogen-free distilled water was injected in the ear vein, and the rectal temperature was measured 3 times at one-hour intervals after injection. A difference between the reference temperature and the maximum temperature was taken as an increase of body temperature, and the pyrogenicity of the test compound was expressed by the number of febrile animals showing a temperature increase of 0.6° C. or more. The results obtained are shown in Table 4.

TABLE 4

| Pyrogenicity | | |
|---|---|---|
| Test Compound | Dose (μg/kg) | Number of Febrile Animals/Number of Tested Animals |
| Compound of Present Invention | 0.1 | 3/4 |
| Control Compound 1 | 0.1 | 0/3 |
| Control Compound 2 | 0.1 | 1/3 |

TABLE 4-continued

| Pyrogenicity | | |
|---|---|---|
| Test Compound | Dose (μg/kg) | Number of Febrile Animals/Number of Tested Animals |
| Control Compound 3 | 0.1 | 1/3 |

Test III—Limulus Test on Pyrogenicity

The pyrogenicity of the compounds of this invention was also determined by Limulus test (toxicolor test). That is, the test compound was dissolved in a pyrogen-free 0.1% (vol/vol) triethylamine aqueous solution to a concentration of 2 mg/ml and diluted with pyrogen-free distilled water to a concentration of $4 \times 10^{-1}$ mg/ml. Subsequently, dilute aqueous solutions having concentrations of from $4 \times 10^{-1}$ mg/ml to $4 \times 10^{-10}$ mg/ml were prepared by serial 10-fold dilution. 0.1 ml of a mixture of 0.1 ml of each dilute aqueous solution, a lyophilized amoebocyte lysate of Tachypleus tridentatus (manufactured by Teikoku Zoki Pharmaceutical Co., Tokyo) and a chromogenic substance, N-t-butoxycarbonyl-L-leucylglycyl-L-alginine-p-nitroaniline, was incubated at 37° C. for 30 minutes in a pyrogen-free reactor. Thereafter, 0.5 ml of sodium nitrite was added to the culture, and after stirring 0.1 ml each of ammonium sulfamate and N-(1-naphthyl)-ethylenediamine were added thereto to develop a color, and absorbance at a wavelength of 545 nm was determined. Based on the determination results, the activity exhibited by 1 mg of each test compound was converted to an amount of an LPS derived from E. coli 0111:B4 (Bacto lipopolysaccharide W; manufactured by Difco). The results obtained are shown in Table 5 below.

TABLE 5

| Limulus Test (Toxicolor Test) | |
|---|---|
| Test Compound | Converted LPS Amount (mg) |
| Compound of Present Invention | 2.38 |
| Control Compound 1 | 1.34 |
| Control Compound 2 | 1.48 |

While the invention has been described in detail and with reference to specific embodiments thereof, it will be apparent to one skilled in the art that various changes and modifications can be made therein without departing from the spirit and scope thereof.

What is claimed is:

1. A process for preparing a disaccharide derivative represented by formula (I)

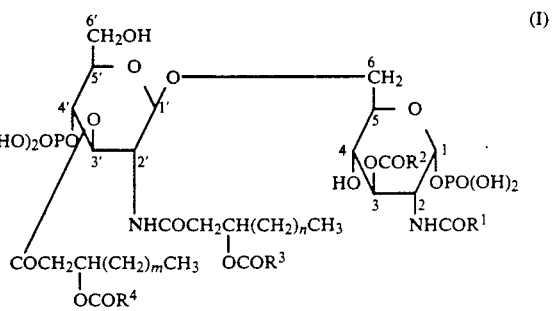

wherein R¹CO— and R²CO— each represents a residue of a straight chain fatty acid having from 8 to 20 carbon atoms and having a hydroxyl group at the 3-position thereof; R³CO— and R⁴CO— each represents a residue of a straight chain fatty acid having from 8 to 20 carbon atoms; and m and n each represents an integer of from 8 to 12, and a salt thereof, comprising A) condensing a compound of the formula (II):

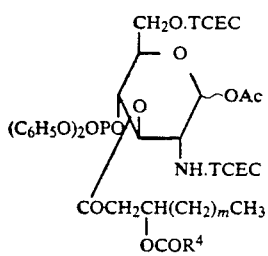

with a compound of formula (III)

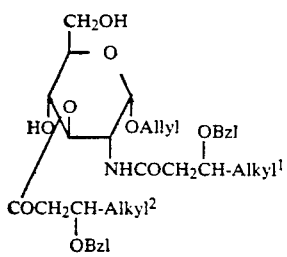

to obtain a compound of the formula (IV)

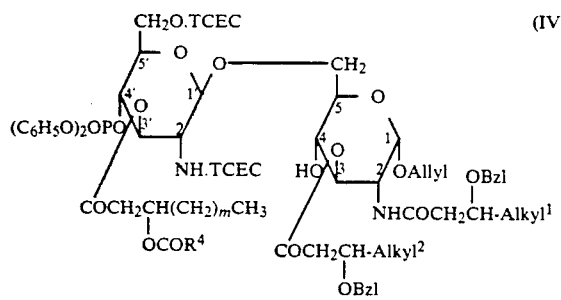

B) removing TCEC groups bonded to the 2'-amino group and the 6-hydroxyl group of compound (IV), and, at the same time, bonding a group represented by the formula (VI)

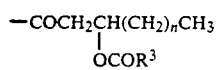

to the 2'-amino group,

C) protecting the 6'-hydroxyl group with a protecting group for hydroxyl group,

D) removing the protecting allyl group at the 1-hydroxyl group to obtain a compound represented by formula (V)

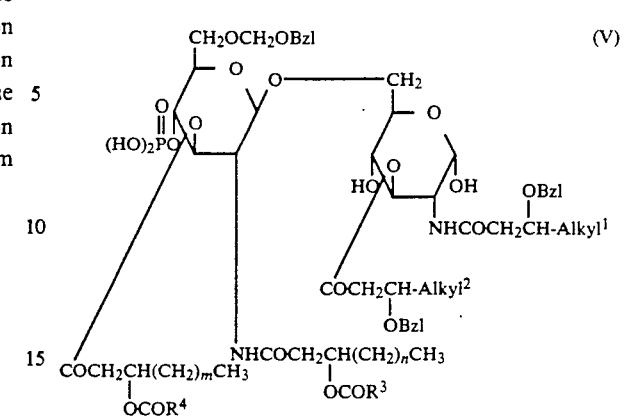

and

E) reacting the compound of formula (V) with dibenzyl phosphorochloridate to introduce a phosphono group into the 1-hydroxyl group, and then removing the benzyl group protecting functional groups by catalytic reduction to obtain the compound of formula (I);

wherein the foregoing formulae TCEC represents a trichloroethoxycarbonyl group; Allyl represents an allyl group; Ac represents an acetyl group; Bzl represents a benzyl group; Alkyl¹ and Alkyl² each represents an alkyl group having from 5 to 17 carbon atoms; and R³CO—, R⁴CO—, and m and n each is the same as defined above for the formula (I).

2. A process for preparing a disaccharide derivative as in claim 1, wherein the compound of formula (I) obtained in step E) is purified by silica gel chromatography and then desalted by electrodialysis.

3. A process for preparing a disaccharide derivative comprising reacting a compound of formula (V)

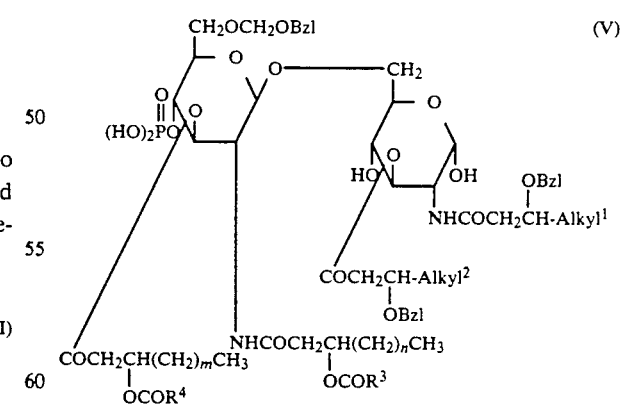

with dibenzyl phosphorochloridate to introduce a phosphono group into the 1-hydroxyl group, and then removing the benzyl group protecting functional groups by catalytic reduction to obtain a compound of formula (I)

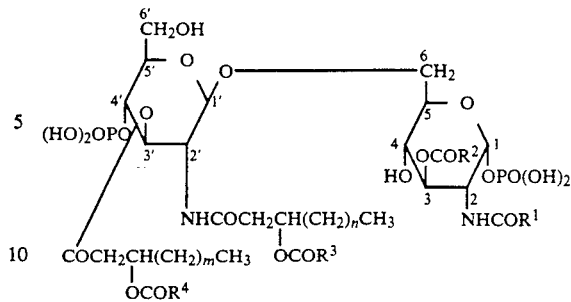

wherein Bzl represents a benzyl group, Alkyl¹ and Alkyl² each represents an alkyl group having from 5 to 17 carbon atoms, $R^1CO-$ and $R^2CO-$ each represents a residue of a straight chain fatty acid having from 8 to 20 carbon atoms and having a hydroxyl group at the 3—position thereof, $R^3CO-$ and $R^4CO-$ each represents a residue of a straight chain fatty acid having from 8 to 20 carbon atoms, and m and n each represents an integer of from 8 to 12, and a salt thereof.

* * * * *

UNITED STATES PATENT AND TRADEMARK OFFICE
CERTIFICATE OF CORRECTION

PATENT NO. : 5,066,794

DATED : November 19, 1991

INVENTOR(S) : TETSUO SHIBA

It is certified that error appears in the above-identified patent and that said Letters Patent is hereby corrected as shown below:

On the title page, please insert, after item [63] and before item [51], the following:

-- [30]     Foreign Application Priority Data

Aug. 24, 1984 [JP]   Japan .................. 59-176328 --.

Signed and Sealed this

Sixth Day of April, 1993

*Attest:*

STEPHEN G. KUNIN

*Attesting Officer*    Acting Commissioner of Patents and Trademarks